United States Patent [19]

Bohuon

[11] Patent Number: 5,639,617
[45] Date of Patent: Jun. 17, 1997

[54] METHOD FOR EARLY DETECTION, DETECTION OF THE SEVERITY AND FOR A TREATMENT-ACCOMPANYING ASSESSMENT OF THE COURSE OF A SEPSIS

[75] Inventor: Claude Bohuon, Paris, France

[73] Assignee: B.R.A.H.M.S. Diagnostica GmbH, Berlin, Germany

[21] Appl. No.: 387,714

[22] PCT Filed: Aug. 19, 1993

[86] PCT No.: PCT/EP93/02245

§ 371 Date: Apr. 17, 1995

§ 102(e) Date: Apr. 17, 1995

[87] PCT Pub. No.: WO94/04927

PCT Pub. Date: Mar. 3, 1994

[30] Foreign Application Priority Data

Aug. 19, 1992 [DE] Germany ............ 42 27 454.0

[51] Int. Cl.⁶ .................................. G01N 33/53
[52] U.S. Cl. .............. 435/7.1; 435/7.94; 424/139.1; 424/158.1
[58] Field of Search ................. 435/7.1, 7.94; 424/139.1, 158.1

[56] References Cited

U.S. PATENT DOCUMENTS 5,424,221 6/1995 Westermark et al. ............ 436/518

FOREIGN PATENT DOCUMENTS 0115459 1/1984 European Pat. Off. .

OTHER PUBLICATIONS

"Calcitron gene-related peptide levels are elevated in patients with sepsis," Surgery 108:1097–1101, 1990; Joyce, et al.

Edbrooke, M R et al, The EMBO Journal, v4, n3, 1985, pp. 715–724.

Cate, C C et al, Cancer Research, v46, Feb. 1986, pp. 812–818.

Coombs, R C et al, The Lancet, Jun. 1, 1974, pp. 1080–1083.

Dietrich, F M et al, ACTA Endocrinologica, v80, 1975 pp. 465–486.

Defros, L J et al, J Clical Endocrinol. Metab., v40, 1975, pp. 409–12.0.

Motte',P et al, Clinica Chimica Acta, v174, 1988, pp. 35–54.

Seth,R et al, Journal of Endocrinology, v119, 1988, pp. 351–357.

Born,W et al, Regulatory Peptides, v32, 1991, pp. 311–319.rgf.

Minvielle, Stephane et al, Journal of Biological Cemistry, v266, n36, Dec. 25, 1991, pp. 24627–24631.

Joyce, C D et al, Surgery, v108, n6, Dec. 1990, pp. 1097–1101.

Gknonos, Peter J et al, The Journal of Biological Chemistry, v261, n31, Nov. 5, 1986, pp. 14386–14391.

Morris, Howard R. et al, Nature, v308, Apr. 1984, pp. 746–748.

Ittner, J et al, J of Clinical Endocrinology and Metabolism, v61, 1985, pp. 1133–1137.

International Search Report, Dated Dec. 3, 1993, Appl. No. PCT/EP93/02245.

P. P. Ghillani, et al., "Identification and Measurement of Calcitonin Precursors in Serum of Patients with Malignant Diseases", Cancer Research, vol. 49, No. 23, Dec. 1, 1989, pp. 6845–6851.

P. P. Ghillani, et al., "Monoclonal antipeptide antibodies as tools to dissect closely related gene products", The Journal of Immunology, vol. 141, No. 9, Nov. 1, 1988, pp. 3156–3163.

M. Assicot, et al., "High serum procalcitonin concentrations in patients with sepsis and infection", The Lancet, vol. 341, No. 8844, Feb. 1993, pp. 515–518.

J. M. Conlon, et al., "Structural characterization of a high–molecular–mass form of calcitonin . . . ", The Biochemical Journal, vol. 256, No. 1, Nov. 15, 1988, pp. 245–250.

A. Meurant, et al., "Immunoreactive hypercalcitoninemia in fulminant meningococcaemia in children cited in a the application", vol. 18, No. 8, Aug. 1984, p. 811.

Primary Examiner—James C. Housel
Assistant Examiner—Ginny Allen Portner
Attorney, Agent, or Firm—Fish & Richardson P.C.

[57] ABSTRACT

Disclosed is a method for early detection, detection of the severity as well as for a treatment-accompanying assessment of the course of a sepsis as well as means for carrying out said method. According to the invention, the content of the peptide procalcitonin and/or of a partial peptide formed therefrom which is not the mature calcitonin is determined in a sample of a biological liquid of a patient. From the determined presence and amount of the certain peptide, a conclusion is made about the presence of a sepsis, its severity and/or the success of a therapeutic treatment.

15 Claims, No Drawings

METHOD FOR EARLY DETECTION, DETECTION OF THE SEVERITY AND FOR A TREATMENT-ACCOMPANYING ASSESSMENT OF THE COURSE OF A SEPSIS

The invention relates to a method for sepsis diagnosis, in particular to early detection and detection of the severity of a sepsis as well as for a treatment-accompanying survey of the therapeutical success of a sepsis treatment which is based on the new knowledge that a certain peptide known per se and possibly certain of its fragments represent reliable biological markers for diseases of this kind appearing in high concentrations and which may be determined relatively simple according to classical detection measures.

According to a more modern understanding of this disease, the term "sepsis" as used in the present application summarizes clinical pictures, for which, as a rule, fever, leucocytosis, consciousness changes, a hyperdynamic circulation ("warm shock"), and a hyper-metabolic status, mainly as a consequence of the invasion of the normally sterile tissue by microorganisms, are observed, whereas the positive detection of germs in the blood, which was previously understood to be a characteristic for a sepsis, has become less important for the diagnosis "sepsis". For in clinical studies it could be shown that the prognosis of patients with sepsis is not dependent on the severity of an infection, in particular a bacterial infection, but on the severity of the septic reaction of the organism (see G. Pilz, S. Fateh-Moghadam and K. Werdan in: Krankenpflege-Journal 29 (1991), pp. 483–492 and publications cited therein). Accordingly, in addition to the positive blood culture or instead of it, for a sepsis assessment at present various laboratory parameters and hemodynamic parameters are determined and taken into account for making a diagnosis and assess the course of the disease, if necessary, using computer-aided so-called Score systems, such as the APACHE (Acute Physiology and Chronic Health Evaluation) II Score described in the above-indicated publication. However, so far no individual parameter suitable as a reliable biological marker is known, the determination of which is highly expressive for a sepsis diagnosis. All parameters used up to now have either an insufficient specificity or do not allow a reliable assessment of the severity of a sepsis and no therapy survey and, in addition to this, the determination of substances, such as the tumor necrosis factor (TNF), or interleukines, such as interleukin 6 (IL-6), is much too complicated, expensive and/or time-consuming for a bedside determination.

Therefore, there is still an urgent need of a reliable biological marker which can be determined relatively easy and the qualitative and particularly quantitative determination of which is highly indicative for making a diagnosis and assessing the progression of a sepsis.

It is the object of the present invention to provide a method for early detection and for detection of the severity of a sepsis wherein a new biological marker is determined in a way which is also practicable under clinical conditions, the determination of which gives highly relevant results for making a diagnosis and assessing the progression of a sepsis.

This object has been achieved by a method and means according to the claims. The invention is based on the surprising finding that the peptide procalcitonin known per se and, if necessary, certain of its higher molecular cleavage products, represent highly relevant biological markers for sepsis and that their concentrations in samples of biological liquids of patients allow highly relevant conclusions on the severity of a septic disease and, thus, represent valuable parameters for the progression assessment and therapy survey of a sepsis.

Therefore, the possibility of a sepsis diagnosis by determination of the peptide procalcitonin is of a great practical interest, since other known possible biological markers appearing in the case of sepsis, such as certain cytokines (interleukines, TNF) represent unstable molecules which normally are present only in very small concentrations, so that their determination is much too complicated, time-consuming and thus expensive for a routine bedside diagnosis. As could be determined according to the present invention—completely surprising with respect to the previous medical knowledge—the procalcitonin content is enormously elevated in the case of a sepsis, so that concentrations in the ng range (above 1 ng, in particular above 10 ng up to 500 ng and more per ml serum or plasma sample) are obtained, whereas for healthy persons with the known best methods of procalcitonin determination no procalcitonin content can be detected (concentrations below 0.1 ng/ml sample). At the same time in the case of a sepsis no increased calcitonin concentrations are observed according to the invention, which is remarkable for the reason that up to the present, as a rule, procalcitonin was regarded as calcitonin precursor, the appearance of which also leads to a calcitonin formation.

The peptide procalcitonin to be determined with the method according to the invention and its possibly appearing proteolytic cleavage products are known, and determination methods suitable for a quantitative and qualitative immunodiagnostic determination are also known.

Procalcitonin is a peptide of 116 amino acids, and up to the present it was known about it that it appears as an intermediate of the translation/expression of a certain gene (CALC-1), leading to the formation of the peptide hormone calcitonin, in a plurality of tissues, in particular in the thyroid C cells and in tumor tissue, as precursor of calcitonin, with this original gene (CALC-1), apart from the formation of procalcitonin also controlling the formation of procalcitonin-gene-related peptide, and distinctly differing from it by its length and in the sequence of the amino acids 51 to 116 of the procalcitonin (see J. Biol. Chem., 261, 31(1986), pp. 14386–14391).

According to the general knowledge, procalcitonin is a proteolytical degradation product of the primary protein preprocalcitonin formed by one certain type of gene expression of the gene CALC-1, and in the known cases of its appearance, as a rule, undergoes a further stepwise degradation under release of mature calcitonin which corresponds to a sequence of 32 amino acids (amino acids 60 to 81 of the procalcitonin). Among others, in this process at first two larger peptides are formed which may be designated N-procalcitonin-(1–57)-peptide, and C-procalcitonin-(60–116)-peptide, with the latter peptide being further splittable to the hormones calcitonin and to the peptide known as katacalcine (Biochem. J. 256, (1988) 245–250; and Cancer Research 49 (1989), 6845–6851). From J. Biol. Chem. 226, 36, pp. 24627–24631 it has recently been known that, apart from the procalcitonin described in the above publications, also a variant of the procalcitonin is formed in human thyroid C cells which differs from the first by the last 8 amino acids of the C terminus. Also this peptide is to be regarded as "procalcitonin" in the sense of the present invention, since at present the immunodiagnostical determination methods used in the development of the present invention do not allow to differentiate between the two procalcitonins and possible other closely related peptides.

Therefore, "procalcitonin" in the sense of the present invention stands for one or a plurality of peptides including the known molecule procalcitonin, the above-described variant thereof, having an amino acid composition deviating therefrom at the C terminus and possible further existing variants with a comparable reactivity in the selective immunodiagnostical determination methods used for their determination, in particular in the monoclonal immunoradiometric assay described in the following with reference to the publication Cancer Res. 49, (1989), 6845–6851.

All these peptides contain peptide sequences of 57 amino acids or more, in particular 116 amino acids like the complete procalcitonin, and correspond to the known sequence or represent partial sequences thereof, with deviations in the region of the amino acids which correspond to the amino acids 108 to 116 of the procalcitonin being possible.

Concerning the previous trials to use the detection of calcitonin and related peptides for diagnostic purposes, it is known that calcitonin is a valuable biological marker (tumor marker) for numerous malignant diseases, and a plurality of immunodiagnostical determination methods has already been developed for the specific determination of calcitonin which methods are carried out using specific monoclonal antibodies (see, for example, Clinica Chimica Acta (1988) 174, pp. 35–54; Immunol., Vol. 141, pp. 3156–3163; J. Endocr. (1988) 119, pp. 351–357).

Also for determining calcitonin precursors, such as procalcitonin and C-procalcitonin-(60–119)-peptide, an immunodiagnostic determination method was already developed which works according to the principle of an immunoradiometric assay (IRMA) and which, apart from calcitonin, allows to selectively determine procalcitonin in that a pair of monoclonal antibodies is used, one of which is specific for regions external of the calcitonin sequence (the amino acids 1 to 11 of the katacalcin or the amino acids 96 to 107 of the procalcitonin), and which is used, for example, in an immobilized form for the extraction of peptides from the analysis sample containing this sequence, whereas the second marked monoclonal antibody, used for forming the IRMA sandwich, is specific for the region corresponding to the amino acids 11 to 17 of the calcitonin (amino acids 70 to 76 of the procalcitonin). In this manner in the immunoassay only those peptides are detected which have the calcitonin regions as well as the amino acids 1 to 11 of the katacalcin region and thus represent either a complete procalcitonin or a peptide with the indicated areas obtained therefrom, such as the C-procalcitonin-(60–116)-peptide (see Cancer Res. 49 (1989), pp. 6845–6851). From the plurality of monoclonal antibodies being available those have been selected (designations mAbKC01 and mAbCT08) in the known method which had association constants in the range of $K_{asn}=0.9–3.0\times10^{10}$ $M^{-1}$. This known method may be used for the determination method according to the invention directly or by using similar monoclonal antibodies which can be obtained on the basis of the disclosure in J. Immunol., Vol. 141, No. 9, (1988), pp. 3156–3163, in which for a determination defining the procalcitonin increase in a particularly clear and easily evaluable way for clinical purposes pairs of antibodies should be used which have similar high affinities as those described above.

For example, pairs of monoclonar antibodies useful for the method of the invention can be produced by using CT-TT (Calcitonin-Tetanustoxoid) as immunogen according to previously described immunization procedures (Motte et al., J. Immunol. 138 (1987), 3332) for the production of antibodies having binding characteristics similar to that of CT21. Antibodies having binding characteristics similar to that of KC01 can be obtained by immunizing Biozzi high responder mice (Biozzi et al., J. Exp. Med. 132 (1970), 152) with KC-TT (katacalcin-tetanustoxoid) whereby according to the procedure described four injections are used consisting of 15 μg of peptides each by different routes; s.c. in Freund's complete adjuvant (FCA), s.c. in Freund's incomplete adjuvant (FIA), i.p. in FIA and i.v. in 0.15 mol/l sodium chloride. The immunization schedules span 13 to 30 weeks. 3 days after the last i.v. injection of the conjugate the mice are sacrificed, the spleen is removed and splenocytes are fused with the NS1 mouse myeloma cell-line by using 40% polyethylene glycol (Bellet et al., J. Clin. Endocrinol. Metab. 56 (1983), 530). The hybridoma supernatants can be screened for specific antibody production by using an ELISA assay. After cloning by limiting dilution, the hybrid cells are implanted i.p. in BALB/c nude (nu/nu) mice and the resulting ascites fluids are collected after 10 to 14 days. The monoclonal antibodies can be purified from the ascites fluids using 50% ammonium sulfate precipitation at 4° C. and protein A chromatography as described in Manil et al. (J. Immunol. Methods 90 (1986), 25). The haptene-carrier conjugates CT-TT or KC-TT can be prepared by separately linking CT or KC to TT by using glutaraldehyde as a coupling agent (Audibert et al., Proc. Natl. Acad. Sci. U.S.A. 79 (1982), 5042).

For the determinations described in the following examples, a pair of monoclonal antibodies has been used which included the above-indicated antibody mAbKC01 and an antibody mAbCT21, with the antibody mAbCT21 regarding its binding to the procalcitonin molecule as well as regarding its affinity being very similar to the antibody mAbCT08 described in the above publication (association constant $K_{asn}=3.0\times10^{10}$ $M^{-1}$). Hybridomas producing the monoclonal antibodies KC01 and CT21 were deposited at "DSM—Deutsche Sammlung von Mikroorganismen and Zellkulturen GmbH", Mascheroderweg 1B, 38124 Braunschweig, Germany, according to the provisions of the Budapest Treaty under deposit numbers DSM ACC2124 and DSM ACC2125, respectively, on Apr. 20, 1993.

The described method according to Cancer Res. 49, (1989), pp. 6845–6851, provides concentration values of the content of a procalcitonin or the C-procalcitonin-(60–119)-peptide or of both of them in samples or, if the stabilities of both peptides are comparable, a value for the initial total concentration of the procalcitonin in the sample. With respect to methods which may be used for determining procalcitonin in accordance with the present invention, we explicitly refer to the above-mentioned publication and the publications cited therein, the contents of which are included in the present application by reference for supplementing the disclosure of the present application.

In the above-indicated publication, the attempt was made to carry out the determination of procalcitonin in order to check its suitability as tumor marker. It has been established that the procalcitonin and calcitonin levels in tumor patients were of parallel behaviour from which the conclusion was drawn that both were derived from neoplastic C cells from the thyroid. In the above-mentioned publication it was further established that the procalcitonin levels were also increased in patients who did not suffer from malignant diseases, but from certain serious virus infections. In these cases, the calcitonin levels were not simultaneously elevated. These patients were not septic patients and their diseases did not have any relation to sepsis diseases.

After it was surprisingly established according to the present invention that there is a close correlation between the procalcitonin levels and the presence and severity of a sepsis, additional considerations were made about the cause of the increase of the procalcitonin level without a simultaneous increase of the calcitonin level in the case of sepsis as well as—to a clearly smaller extent which allows it in most cases to directly distinguish these cases over sepsis—in patients suffering from certain serious virus diseases. Since in one patient with sepsis who underwent total thyroidectomy, nevertheless the increase of the procalcitonin to a level significant for a sepsis could be detected, it was clear that in the case of sepsis the procalcitonin is not formed in the thyroid, but that another organ is competent for it. If with respect to the increased procalcitonin level in the case of virus hepatitis as a working hypothesis it is assumed that this other organ is the liver, the increase of the procalcitonin level could be explained in the first case as a direct effect of the virus disease on the hepatocytes and in the other case as an indirect, but more effective influence of the endotoxines produced by the bacteria responsible for the sepsis on the same hepatocytes. However, it has to be underlined that this ex-post explanation represents a working hypothesis and not a theory proven by experiments.

The appearance of increased procalcitonin levels in the case of serious virus diseases has the effect for the method for sepsis diagnosis according to the invention that, if the procalcitonin levels are elevated only to a relatively small extent up to such values which can also be found in cases of serious virus diseases, the presence of such a virus disease must be excluded before a sepsis diagnosis is made.

Further, in patients with chronic renal failure and therefore disordered peptide excretion it should perhaps be expected that the levels of peptides like procatcitonin are elevated, but that this elevation does not have the same clinical relevance as it is the case in patients which are healthy in this respect. However, the physician establishing the clinical diagnosis can easily take into account these circumstances.

The present invention is not restricted to a use of the above-described known special determination method for the determination of procalcitonin, but includes also other determination methods known per se, to which belong also those methods using other monoclonal or polyclonal antibodies, for example, those methods working with a specificity for the N-procalcitonin-(1–57)-peptide and, in particular, its amino acids 51 to 57. Thus, it could be shown for a common use of polyclonal antibodies against regions of the N-procalcitonin-(1–57)-peptide instead of mAbKC01 together with the marked monoclonal antibody binding to the calcitonin region of the procalcitonin used in the described method that in both cases analogous concentration values were obtained for the procalcitonin content which, on the basis of the fact that, if the indicated polyclonal antibodies are used, the detected regions are present within one molecule only in the case of the intact procalcitonin peptide, suggests the conclusion that in the case of a sepsis the levels of the intact procalcitonin are in fact elevated and the partial peptides formed thereof are of secondary importance at the most.

In principle, the method according to the invention may be carried out also by determining the procalcitonin in a way other than immunodiagnostic, for example, by means of HPLC, if such methods providing sufficient sensitivity and specificity exist or can be developed.

Although moreover the determination of the procalcitonin according to the invention is carried out at present mainly in serum or plasma samples, the method according to the invention in principle includes also determinations of procalcitonin in other biological fluids, such as whole blood and urine, if it should turn out that also in these fluids procalcitonin levels can be measured in a reproducible manner.

Concerning the state of the art it is additionally indicated that in Surgery, Vol. 108, 6 (1990), pp 1097–1101, it is reported that in patients with sepsis the plasma level of the peptide CGRP, which is related to calcitonin, was slightly elevated in the pg range (14.9+3.2 pg/ml compared to 2.0+0.3 pg/ml in control persons). These findings do not allow to draw any conclusion about the levels of other, related peptides, and the significantly lower absolute concentrations and significantly lower relative increases in the case of sepsis in comparison with the normal concentration compared to the increase in the method according to the invention suggest that the determination of CGRP as sepsis marker is not suitable.

Further, in Lancet 1, (1983), p. 294 it has been reported that in the case of serious meningococcaemia in children the observed calcitonin levels were raised two times to three times, however, in a following publication in Pediatr. Res. 18, (1984), p. 811 it was corrected that the determined substance probably is not the intact calcitonin, but no indication was made what substance was actually measured. The observed increase to approximately three times the normal value in the described cases has to be compared with an increase of procalcitonin in the method according to the invention in the range of a 1000-fold increase, which shows that the indicated publications do not represent a disclosure relevant for the present invention.

The method according to the invention will now be described in more detail with reference to clinical data producing evidence for the relevance of the delivered information.

All procalcitonin determinations have been carried out according to the method of determining procalcitonin described in Cancer Res. 49, (1989), pp 6845–6851, using the monoclonal antibodies KC01 (DSM ACC2124) and CT21 (DSM ACC2125) (see above).

The examples illustrate the invention but should not be construed as limiting the invention.

EXAMPLE 1

Determination of the procalcitonin levels in children hospitalized for various diseases The procalcitonin levels (pCT) of different groups of children hospitalized for various diseases have been determined.

The results are summarized in Table 1.

It may be seen that in sepsis patients up to 180 ng/ml pCT (procalcitonin level) were obtained, whereas the pCT values for "normal" virus diseases maximally increased to 2 ng/ml, only for extremely serious virus diseases of intestine and liver the values raised to 16 ng/ml and in one case to 35 ng/ml

TABLE 1

Serum levels of pCT in children with bacterial and viral infections

| Group | Age (yr) | pCT (ng/ml) | Clinical Details |
| --- | --- | --- | --- |
| Controls (n = 20) | 0.3–10 | <0.1 | Children hospitalized for various diseases with no infections |

TABLE 1-continued

Serum levels of pCT in children with bacterial and viral infections

| Group | Age (yr) | pCT (ng/ml) | Clinical Details |
|---|---|---|---|
| Bacterial infection children (n = 7) | 0.5–8.5 | 16–180 | 5 with meningitis (3 hemophilus, 2 meningococcus), 1 with pulmonary pneumococcosis, 1 with staphylococcia and Steven-Johnson's syndrome |
| Newborn (n = 6) | NN | 13–160 | 6 newborn with positive blood culture (*Escherichia Coli*, Streptococcus B, enterobacter, listeria) |
| Viral infection | | | |
| (n-10) | NN-9 | <0.1–2.0 | 3 with Lymphocytic Meningitis 7 with various viral infections (elevated interferon) |
| (n = 3) | 0.1–5 | 1.1–16 | 2 with rotavirus 1 with coronavirus infections |
| (n = 3) | 2–5 | 1.5–35 | All with hepatitis A |
| Congenital toxoplasmosis (n = 6) | NN | <0.1 | All with subclinical disease |

EXAMPLE 2

Correlation of the pCT levels in patients with sepsis, for whom the course of the disease has simultaneously been observed according to the APACHE II Score, with the severity of their illness In 20 septic patients who have been treated by an i.v. Pseudomonas-IgG sepsis therapy after cardiac operations, the pCT levels have been observed for five days with their illness state simultaneously being evaluated according to the APACHE II Score. The results are summarized in the following Table 2.

From Table 2, it may be clearly taken that in the case of response to a successful sepsis therapy (Responder) the pCT levels decreased with the improvement of the clinical status, whereas they remained nearly unchanged high in the case of non-response (Non-Responder) to the treatment. It may also be seen that in the case of non-responders, the initial pCT levels were significantly higher than those of the responders and thus, the illness severity of the former was greater. As compared with the values of the APACHE II Score, the pCT values significantly clearly represent the different severity grades of the sepsis, which is also confirmed by the lethality figures.

These results show further that the accompanying determination of pCT level during a sepsis treatment at an early state gives reliable information on the treatment success, so that if necessary, an early decision in respect of a change of the selected treatment, for example, the selection of another antibiotic preparation is possible.

Similar results could also be derived in the case of burn patients, in whom a sepsis developed in connection with skin transplantations, which were treated with various antibiotic preparations. A treatment success was always accompanied by a significant decrease of the pCT concentration, and in one case it was possible to early correct non-response to a first treatment with a first antibiotic preparation—which could be detected since the pCT concentrations remained constant—by changing the antibiotic preparation with the response to the second antibiotic preparation being recognizable in that the pCT level dropped immediately.

I claim:

1. Method for early detection of a sepsis in a patient in need thereof comprising: determining in a sample of a biological liquid of a patient the concentration of procalcitonin, the determined presence and amount of procalcitonin being indicative of the presence of a sepsis.

2. The method according to claim 1, characterized in that procalcitonin and N-procalcitonin (amino acids 1–57)-peptide and C-procalcitonin-(amino acids 60–116)-peptides are determined.

3. Method according to claim 1 or 2, characterized in that the corresponding peptide or peptides are determined in an immunodiagnostic method by use of a monoclonal antibody

TABLE 2

| | Day 1 | Day 2 | Day 3 | Day 5 |
|---|---|---|---|---|
| APACHE II Score | | | | |
| Responder (n = 11) | 26 ± 1 | 24 ± 2 | 23 ± 3 | 16 ± 1 |
| Non-Responder (n = 9) | 28 ± 2 | 31 ± 2 | 31 ± 2 | 29 ± 1 |
| pCT | | | | |
| Responder (n = 11) | 87 ± 33 | 87 ± 37 | 104 ± 41 | 22 ± 7 |
| Non-Responder (n = 9) | 259 ± 56 | 278 ± 62 | 214 ± 68 | 181 ± 66 |
| Lethality | | | | |
| Responder (n = 11) | 9% | | | |
| Non-Responder (n = 9) | 56% | | | |

$\bar{x} \pm$ SEM
1 $p < 0.05$ (M-W)
2 $p < 0.05$ (Wilcoxon)
3 $p < 0.05$ (Chi$^2$)

or a combination of a first monoclonal or polyclonal antibody with a second monoclonal antibody, which as such or combined with each other have a specificity for procalcitonin or peptides formed therefrom, and which allow to differentiate between them and mature calcitonin and the CGRP peptide.

4. Method according to claim 3, characterized in that procalcitonin is determined by means of an immunometric assay wherein for binding the procalcitonin from the sample a first monoclonal antibody is used binding the procalcitonin in another region as the second monoclonal antibody used for marking, so that a differentiation between procalcitonin and its proteolyic degradation products including calcitonin is possible.

5. Method according to claim 4, characterized in that, apart from the first monoclonal antibody, for binding procalcitonin at least one further monoclonal antibody is used which binds the procalcitonin molecule in another region.

6. Method according to claims 1, characterized in that procalcitonin is determined by means of an immunometric assay which selectively detects the complete procalcitonin and C-procalcitonin-(60–116)-peptide, if present.

7. Method according to claim 1, characterized in that procalcitonin is determined by means of an immunometric assay which selectively detects the complete procalcitonin and N-procalcitonin-(1–57)-peptide.

8. Method according to claim 6, characterized in that procalcitonin contents of more than 1 ng/ml sample are indicative of the possible presence of a sepsis and that procalcitonin contents in the range of 10 ng/ml to 500 ng/ml and higher correlate with an increasing severity of the sepsis and a worsened prognosis.

9. Method according to claim 8, characterized in that simultaneously in a parallel determination the calcitonin level is determined and that the absence of evidence for elevated calcitonin levels allows the sepsis diagnosis to be made.

10. Method according to claim 8 or 9, characterized in that procalcitonin levels in the range of approximately up to 20 ng/ml allow the sepsis diagnosis to be made, if the presence of a serious virus disease as a reason for the elevated procalcitonin level can be excluded.

11. Method according to claim 1, characterized in that a serum or plasma sample is used as the sample of a biological liquid.

12. Method according to claim 1, characterized in that the monoclonal antibody is the monoclonal antibody KC01 (DSM ACC2124) or the antibody CT21 (DSM ACC2125).

13. The method of claim 1 wherein the amount of the peptide detected indicates the severity of the sepsis or the success of a therapeutic treatment.

14. The method of claim 13 wherein the antibody is selected from the group consisting of monoclonal antibodies KC01 and CT21.

15. The method of claim 1, wherein the concentration of procalcitonin is determined immunologically.

* * * * *